US011963897B2

(12) United States Patent
Hinshon

(10) Patent No.: US 11,963,897 B2
(45) Date of Patent: Apr. 23, 2024

(54) EXTENSION CONTROL MEMBER FOR USE WITH AN ANKLE-FOOT ORTHOSIS

(71) Applicant: Orthotic Care Services, LLP, Minneapolis, MN (US)

(72) Inventor: Patrick Scott Hinshon, Maplewood, MN (US)

(73) Assignee: Orthotic Care Services, LLP, Minneapolis, MN (US)

( * ) Notice: Subject to any disclaimer, the term of this patent is extended or adjusted under 35 U.S.C. 154(b) by 0 days.

(21) Appl. No.: 16/959,613

(22) PCT Filed: Feb. 19, 2019

(86) PCT No.: PCT/US2019/018654
§ 371 (c)(1),
(2) Date: Jul. 1, 2020

(87) PCT Pub. No.: WO2019/161416
PCT Pub. Date: Aug. 22, 2019

(65) Prior Publication Data
US 2020/0383815 A1 Dec. 10, 2020

Related U.S. Application Data

(60) Provisional application No. 62/710,404, filed on Feb. 16, 2018.

(51) Int. Cl.
*A61F 5/01* (2006.01)
(52) U.S. Cl.
CPC .... *A61F 5/0127* (2013.01); *A61F 2005/0165* (2013.01)
(58) Field of Classification Search
CPC .... A61F 5/0113; A61F 5/0127; A61F 5/0111; A61F 5/01; A61F 2005/0165;
(Continued)

(56) References Cited

U.S. PATENT DOCUMENTS

| 5,486,157 A | 1/1996 | DiBenedetto |
| 6,302,858 B1 | 10/2001 | Detoro et al. |

(Continued)

FOREIGN PATENT DOCUMENTS

| DE | 3720767 A1 | 1/1988 |
| WO | 02065942 A2 | 8/2002 |

(Continued)

OTHER PUBLICATIONS

Kerrigan Priority Document for WO-02065942-A2. Obtained from WIPO public website. (Year: 2002).*

(Continued)

*Primary Examiner* — Michelle J Lee
(74) *Attorney, Agent, or Firm* — Craig J. Lervick; Larkin Hoffman Daly & Lindgren, Ltd.

(57) ABSTRACT

An articulated Ankle Foot Orthosis (AFO) with an upper boot member and a lower boot member hinged to one another is made more flexible and effective by having a dorsi-flexion control member attached thereto. The dorsi-flexion control member has a main body with upper portion which is attachable to a predetermined position on the upper boot member, and a lower portion which is attachable to a lower boot member. The main body is fabricated from a material having a predetermined set of elasticity characteristics, which will limit dorsi-flexion movement in a predetermined manner, depending on the material used and the specific configuration. In this manner, the elasticity characteristics of the control member can provide both dynamic and static dorsi-flexion control.

16 Claims, 5 Drawing Sheets

(58) Field of Classification Search
CPC .............. A61F 5/0165; A61F 5/0195; A61F 2005/0153; A61F 2005/0167; A61H 2201/164; A61H 2201/16; A61H 2201/1602; A61H 2201/1642
See application file for complete search history.

(56) References Cited

U.S. PATENT DOCUMENTS

| | | | |
|---|---|---|---|
| 6,824,523 | B2 | 11/2004 | Carlson |
| 7,018,350 | B2 | 3/2006 | Hinshon |
| 7,335,177 | B2 | 2/2008 | Reynolds et al. |
| 9,398,970 | B1 | 7/2016 | Meyer |
| 9,707,118 | B1* | 7/2017 | Meyer .................. A61F 5/0127 |
| 2006/0229542 | A1 | 10/2006 | Sinreich |
| 2006/0270958 | A1* | 11/2006 | George ................ A61F 5/0113 602/23 |
| 2011/0054634 | A1* | 3/2011 | Bartlett .................... A61F 2/60 623/33 |
| 2013/0165833 | A1* | 6/2013 | Blanck .................. A61F 5/0125 602/27 |
| 2014/0039368 | A1* | 2/2014 | Perkins ................. A61F 5/0111 602/12 |
| 2016/0135978 | A1* | 5/2016 | McGovern ........... A61F 5/0127 602/27 |
| 2017/0252197 | A1* | 9/2017 | Hinshon ............... A61F 5/0127 |
| 2019/0192327 | A1* | 6/2019 | Sutti .................... A61H 1/0266 |

FOREIGN PATENT DOCUMENTS

| | | | | |
|---|---|---|---|---|
| WO | WO-02065942 | A2 * | 8/2002 | ........... A61F 5/0111 |
| WO | WO-2015175601 | A1 * | 11/2015 | ............. A47B 97/00 |

OTHER PUBLICATIONS

"International Search Report and Written Opinion", PCT Application No. PCT/US2019/018654, dated Jun. 10, 2019, 16 pages.

* cited by examiner

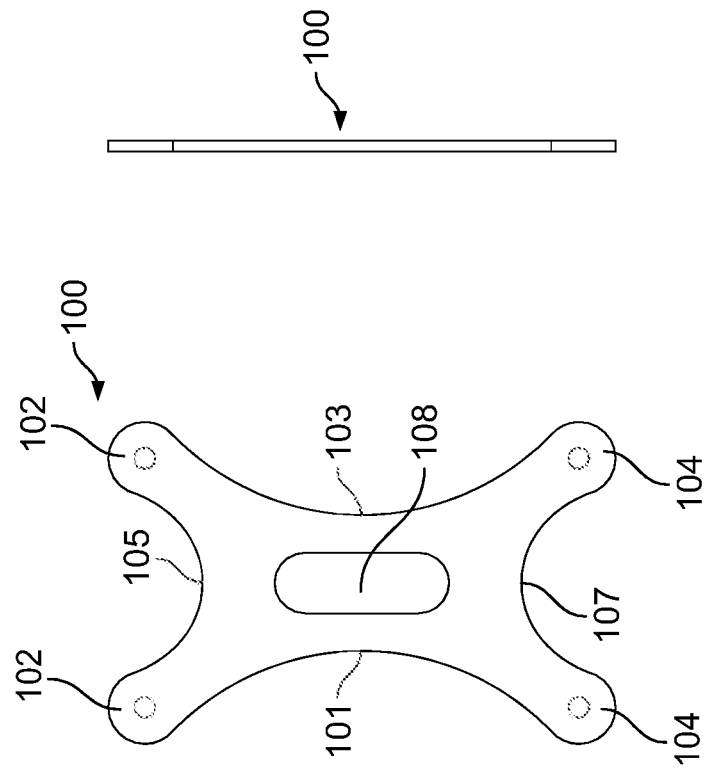
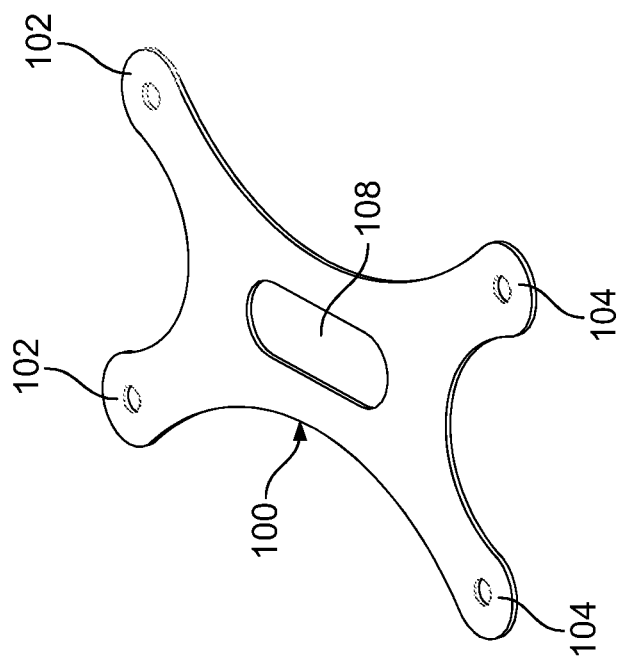

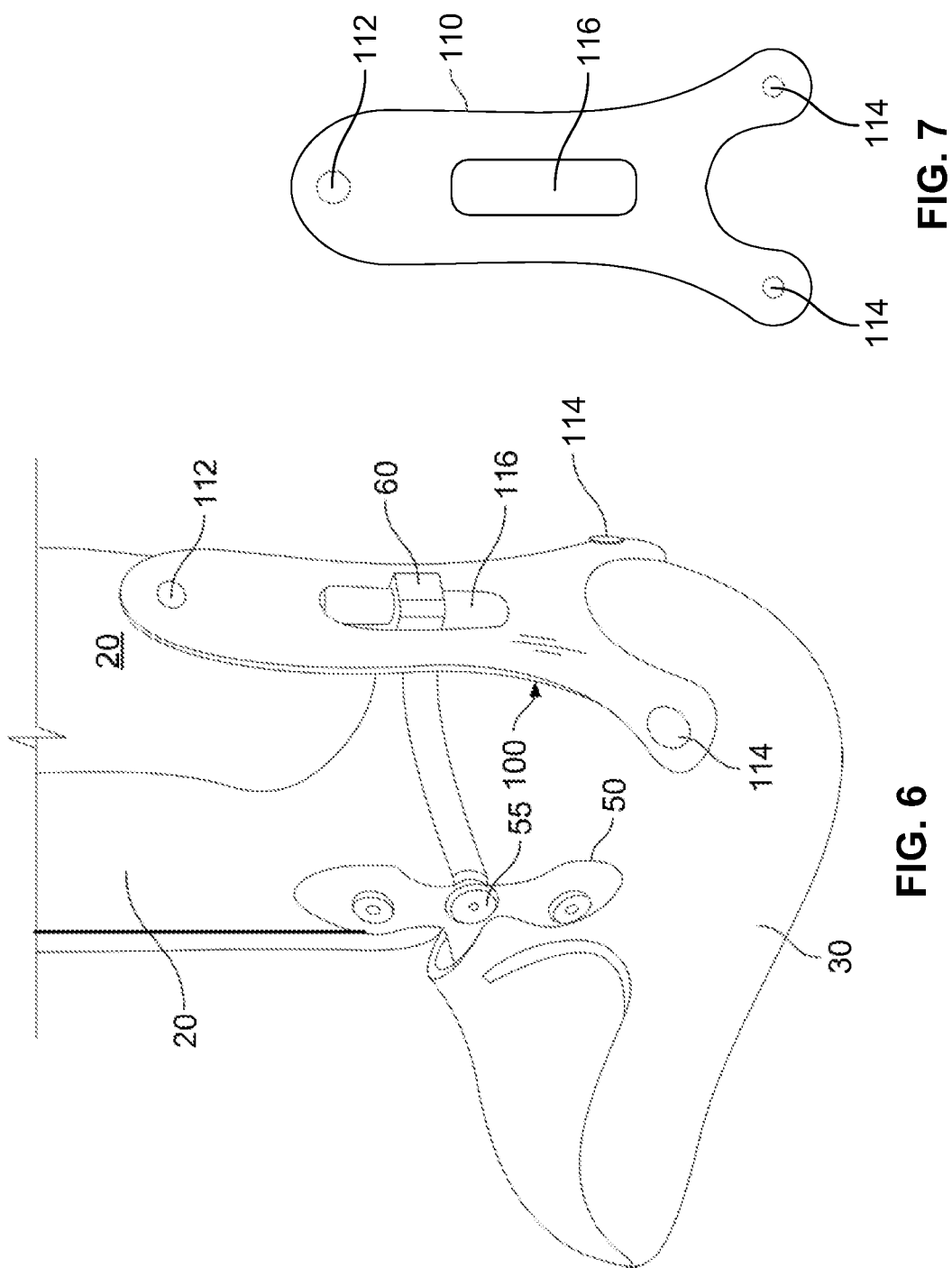

EXTENSION CONTROL MEMBER FOR USE WITH AN ANKLE-FOOT ORTHOSIS

The present application claims the benefit of U.S. Provisional application 62/710,404, filed Feb. 16, 2018, which is incorporated herein by reference. Various details related to Ankle-Foot Orthosis are set forth in U.S. patent application Ser. No. 15/063,079 entitled "Ankle-Foot Orthosis", Published as US 2017/0252197, which is also incorporated herein by reference.

BACKGROUND

The present invention is directed to an improved ankle-foot orthosis, an improved motion control system for the orthosis, methods of making the orthosis and motion control system, materials used to form the orthosis and motion control system, and therapeutic procedures using the orthosis and motion control system.

The human foot is designed so that it can rotate and pivot with regard to the lower leg, as such movements are essential to walking. One primary movement is plantar flexion, which is downward motion of the foot that occurs in the sagittal plane. The opposite movement is dorsi-flexion, which is the upward motion of the foot. In some circumstances it is necessary to limit plantar flexion or dorsi-flexion, depending on the circumstances. For example, individuals with paralysis or weakness of the dorsi-flexion muscle group (which lifts the foot) typically have trouble raising their foot, such as when they're walking. This dorsi-flexion problem can result in tripping and falling as the front of the foot catches on obstacles. Also, individuals with excessive plantar flexion sometimes compensate when walking by lifting their foot and leg higher than normal in order to lift the front of their foot off of the ground. This unnatural lifting of the leg and foot results in a modified gait that is sometimes referred to as a steppage gait because it bears resemblance to the gait of a high-stepping horse.

Alternatively, there are cases where it is necessary to control the level of dorsi-flexion. In the normal walking motion, it is necessary for appropriate muscle groups to resist excessive dorsi-flexion, and spring the foot forward (often referred to as the third phase or rocker phase of the human stride). This resistance and additional "spring effect" thus helps a person complete the final stage of the stride.

Various ankle-foot orthosis devices have been developed to prevent excessive plantar flexion. For example, a solid ankle brace can be placed in an individual's shoe so as to prevent flexing at the ankle joint. These braces may be improved upon by allowing a pivoting movement at the ankle joint to permit the angle between the foot and lower leg to decrease in size, while using a stop to prevent the foot from exceeding a 90 degree angle with the lower leg. These improved articulating orthosis offer significant advantages over prior rigid devices, including improved comfort, allowing a more natural walking motion by the patient, and reducing stiffness by promoting flexing of the ankle joint. That said, many of these devices have certain shortcomings, often do not appropriately resist dorsi-flexion, and/or could be further improved in various ways.

SUMMARY

The details outlined below provide an improved orthosis and improved dorsi-flexion control for the orthosis, which has features and characteristics not previously contemplated. More specifically, the ankle-foot orthosis and dorsi-flexion control system improve on the function and performance of the orthosis, while also making the orthosis attractive and easier to use than prior devices.

The improved orthosis has a compact, adjustable, easily manufactured articulating boot that is both durable and functional. The improved orthosis can include an adjustable stop, which will limit motion (as discussed above). The improved orthosis further includes a dorsi-flexion control mechanism that can be used in conjunction with the stop. When coupled with the ankle-foot orthosis, this dorsi-flexion control mechanism will limit the amount of dorsi-flexion that is possible. The dorsi-flexion control mechanism can be elastic, thus creating a dynamic joint. Similarly, the dorsi-flexion control mechanism can be non-elastic and create a static joint.

Other features and advantages of the invention, including methods of making an orthosis, will be apparent from the following detailed description. The above summary of principles of the disclosure is not intended to describe each illustrated embodiment or every implementation of the present disclosure. The detailed description that follows more particularly exemplifies certain embodiments utilizing the principles disclosed herein.

BRIEF DESCRIPTION OF THE DRAWINGS

Further details and features of the various embodiments will be more fully explained in the following detailed description, with reference to the following drawings, which include:

FIG. 3 is a perspective view of a tension device used in the embodiment of FIG. 2, shown alone;

FIG. 4 is a side view of the tension device shown in FIG. 3;

FIG. 5 is a front view of the tension device shown in FIG. 3;

FIG. 6 is a close up view of an alternative embodiment of the motion control system;

FIG. 7 is a front view of the tension device used in the alternative embodiment of FIG. 6, shown alone;

DESCRIPTION

In order to provide more control and customization options for practitioners, the ankle-foot orthosis (AFO) described herein has the ability to customize operating characteristics to meet a wide range of needs. The AFO is articulated, includes plantar flexion stops to appropriately limit plantar flexion of the user's foot, while also providing dorsi-flexion resistance and/or stops to control dorsi-flexion. In the various embodiments discussed below, a dorsi-flexion control member 100 or 100' is used to provide the desired level of dorsi-flexion control.

Figure 1:
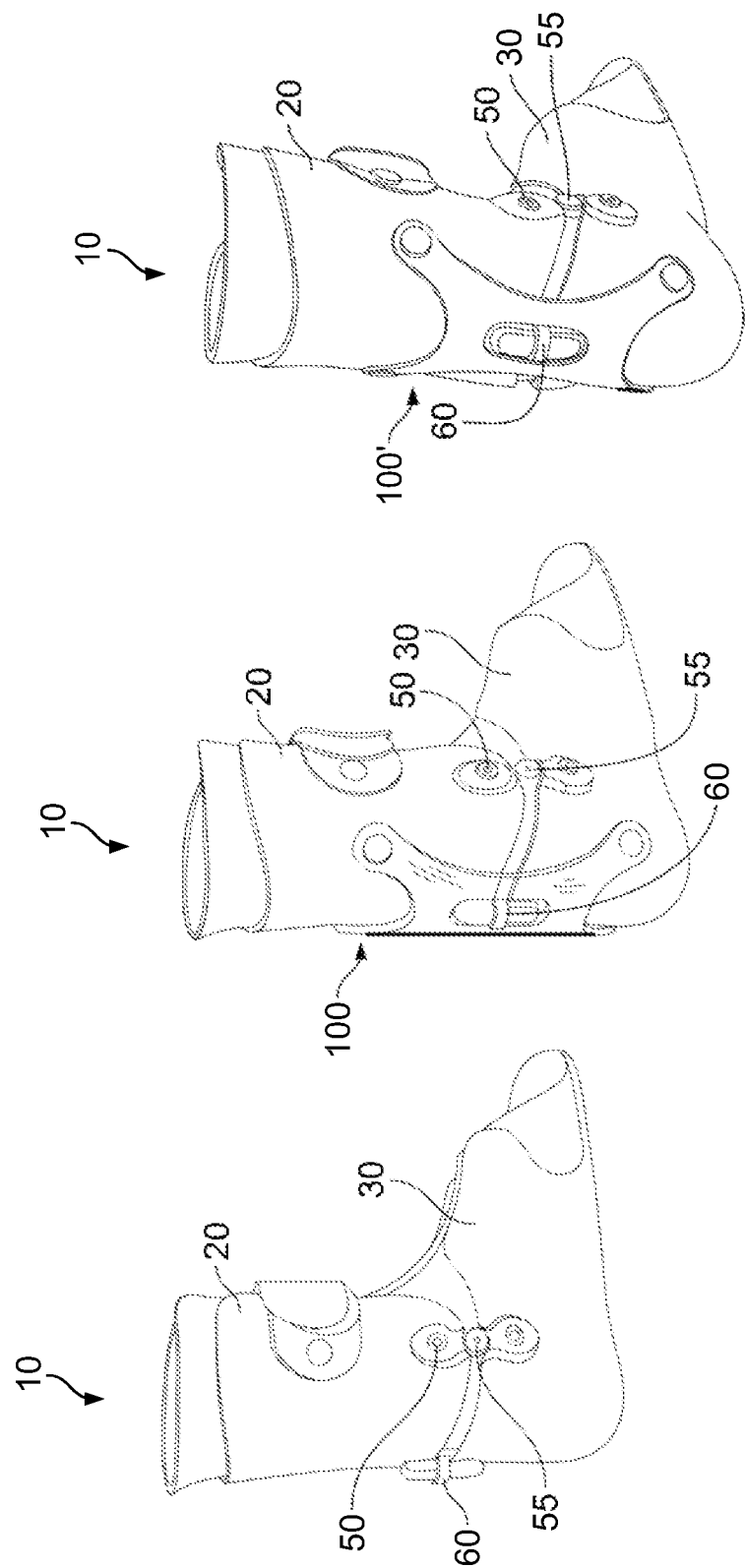
FIGS. 1A-1C shows rear perspective views of three embodiments of an ankle-foot orthosis, with the ankle-foot orthosis of FIGS. 1B & 1C having a dorsi-flexion motion control system incorporated thereon.
Figure 2:
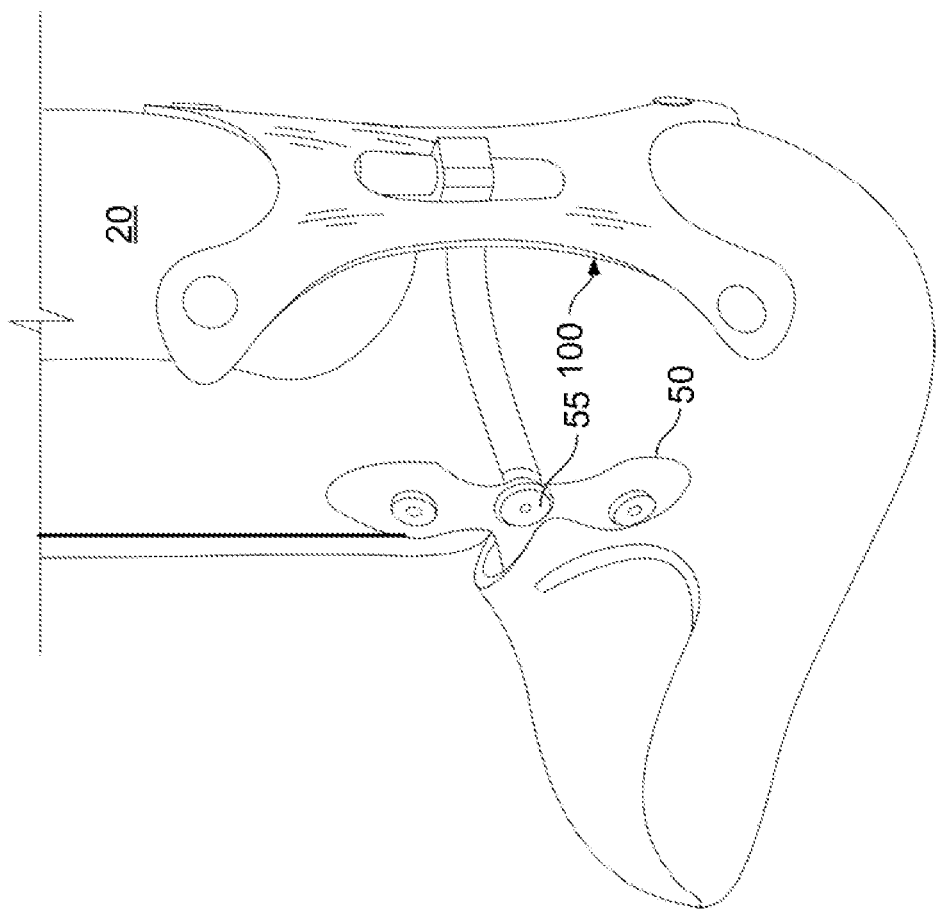
FIG. 2 shows a close up view of one embodiment of the motion control system.

Turning now to the figures, FIG. 1A illustrates an AFO 10\*, which is articulated about a hinge point 55. A joint 50 is provided on each side of AFO 10\* to accommodate articulation of an upper boot member 20 and a lower boot member 30. Further, AFO 10* includes a stop 60 on the back side to provide plantar-flexion stops, as desired. Many different stops 60 could be used, including for example the stop device set forth and described in U.S. Pat. No. 7,018,350, issued in 2006 to the inventor of the present application.

Turning now to FIG. 1B, a similar AFO 10 is illustrated. In this embodiment, AFO 10 again has an articulated upper boot member 20 and a lower boot member 30, which are coupled together by joint 50. Stop 60 is again present to limit the plantar flexion of the user's ankle joint. In addition, AFO 10 includes a dorsi-flexion control member 100, to help control the dorsi-flexion of the user's ankle joint. In this embodiment, dorsi-flexion control member 100 is elastic and is able to provide dynamic control. As shown, a pair of upper arms 102 are coupled to upper boot member 20, while a pair of lower arms 104 are coupled to lower boot member 30. Further details of dorsi-flexion control member 100 are set forth below.

In yet another embodiment, FIG. 1C shows an alternative device. In this embodiment an alternative AFO 10' has an articulated upper boot member 20 and a lower boot member 30. To provide an alternative approach however, a static dorsi-flexion control member 100' is attached at a rear location of AFO 10'. Again, static dorsi-flexion control member 100' has a pair of upper arms 102 are coupled to upper boot member 20, and a pair of lower arms 104 which are coupled to lower boot member 30. In this embodiment, static dorsi-flexion control member 100' is flexible, but non-elastic. In one example embodiment, a urethane coated fabric is used to form static dorsi-flexion control member 100'. In another embodiment, static dorsiflexion control member 100' may be formed from a plastic or composite material. As will be appreciated, these types of materials are generally non-elastic and will not stretch an appreciable amount. As will also be appreciated, this embodiment provides static dorsi-flexion control and essentially allows a practitioner to create a rigid or locked AFO 10'.

Those skilled in the art will recognize that both dynamic dorsi-flexion control member 100 and static dorsi-flexion control member 100' are removable. In practice, this allows a practitioner to fit the AFO for either application, and to convert at any point in time. As one example, an initial prescription may call for a static or rigid AFO, with articulation to be contemplated at a later date. Using the embodiments set forth above, the practitioner can first fit the upper boot member 20, lower boot member 30 and stop 60 to appropriately fit the patient. Next, the static dorsi-flexion control member 100' can be attached, thus providing the prescribed rigid or locked orthosis. As therapy progresses, the dynamic dorsi-flexion control member 100 can be used, thus providing an articulated AFO with controlled dorsi-flexion resistance. Later, removal of dorsi-flexion control member 100 may be appropriate. Regardless of the situation, the same articulated upper boot member 20 and lower boot member 30 can be used, without the need to "re-fit" these components.

Turning now to FIGS. 3-5, detailed illustrations of one embodiment of dynamic dorsi-flexion control member 100 are presented. As mentioned above, dorsi-flexion control member 100 has a pair of upper arms 102 and a pair of lower arms 104, each having attachment holes therein to accommodate the easy attachment to appropriate portions of AFO 10. Control member 100 also has a central opening 108 which is specifically configured to surround stop 60 and provide relief, thereby avoiding interference. In the illustrated embodiment, dorsi-flexion control member 100 is configured in a generally "X-shaped" configuration, having a pair of side indentations 101 & 103, an upper indentation 105 and a lower indentation 107. Although variations are possible, this particular "X-shaped" configuration helps to accommodate attachment, control and support in a both a convenient and efficient manner. More specifically, this configuration allows dorsi-flexion control member 100 to provide support/control in multiple directions. Clearly, dorsi-flexion control member 100 is coupled to both the upper and lower boot, thus providing the desired resistance to the hinged movement of the ankle joint. In use, forward movement of the upper boot member 20 relative to lower boot member 30 and the related rotation about hinge 50 (i.e. dorsi-flexion), will create shear forces on dorsi-flexion control member 100. The materials and configuration of dorsi-flexion control member 100 will naturally resist these forces and provide the desired resistance to the hinged movement of the ankle joint. Additionally, connection points are positioned on either side of a rear centerline of the AFO 10 (i.e. a centerline extending vertically along the back or heal portion of AFO 10), thus providing an evenly distributed level of resistance. This will help to avoid stressing or deflecting portions of the AFO 10 in an undesired manner. As illustrated, the connection points are equidistant from the centerline to evenly distribute the desired resistance. In some embodiments, the connection points are further configured to be generally aligned with a hinge axis of AFO 10. More specifically, it may be beneficial to have the upper connection points be equidistant from the hinge axis. Similarly, the lower connection points will be equidistant from the hinge axis. When this is accomplished, the resistance provided by dorsi-flexion control member 100 will be evenly distributed and symmetrical. In other cases, the connection points can be altered to provide a customized resistance profile. Those skilled in the art will recognize that many variations are possible.

As illustrated in FIG. 4, one embodiment of dorsi-flexion control member 100 is approximately 4.4 inches tall and approximately 2.9 inches wide. This is the typical size used in adult applications. In pediatric applications, dorsi-flexion control member 100 may be approximately three inches (3") tall and approximately two and a half inches (2½") wide. Naturally, these dimensions and the overall configuration of dorsi-flexion control member 100 could change, while still achieving the general goals involved.

In one embodiment, dynamic dorsi-flexion control member 100 is made from an elastomer, such as a silicone-based material. More specifically, it is desirable to have an isotropic polymer with a modulus of elasticity that is proportional to thickness and a high elastic limit. In this case, the thickness of dynamic dorsi-flexion control member 100 can vary as needed to provide the desired elastic characteristics. In some embodiments, this thickness will be in the range of approximately one-sixteenth of an inch (1/16") to approximately one-quarter inch (¼"). The thickness of this material will help to control the elastic characteristics, thus selecting various thicknesses allows the practitioner to further customize the AFO 10. For pediatric patients, this thickness may be in the range of one-sixteenth of an inch (1/16") to one-eighth of an inch (⅛"). Alternatively, for adult patients, the thickness could range from one-eighth of an inch (⅛") to one-quarter inch (¼"). Naturally, these dimensions could also change depending on the circumstances, while still making use of the principles outlined above.

Both static dorsi-flexion control member 100' and static dorsi-flexion control member 100 have certain elastic characteristics. As discussed above, static dorsi-flexion control member 100' is designed to be substantially inelastic, while the elastic characteristics of dynamic control member 100 can vary depending on dimensions, configuration and materials used. Clearly, these characteristics can be specifically chosen to meet the needs of the particular application. That said, this also provides a practitioner many options and often results in a more effective/efficient AFO for use by the patient.

Although it has generally been mentioned, when dynamic dorsi-flexion control member 100 is used, a variable amount of dorsi-flexion resistance is provided. This will clearly help if strength issues are involved. Those skilled in the art will also appreciate that this dynamic control will provide additional energy and power to the user when going through the various stages of the walking motion. In many cases, this will help the user develop a normal gate, and more controlled walking motion.

In the embodiments illustrated above, both static dorsi-flexion control member 100' and dynamic dorsi-flexion control member 100 are configured in a general X-shaped configuration. As illustrated in FIGS. 6-9, alternative embodiments are possible. More specifically, FIGS. 6 & 7 show a similar dorsi-flexion control member 110, which is configured in an "inverted Y-shaped" configuration. As shown, dorsi-flexion control member 110 has two connection points 114 at a bottom portion thereof, which are connectable to the lower boot member 30. Similarly, a single upper connection point 112 is position at an upper end of the inverted Y-shaped body. As also illustrated, an opening 116 is provided so that stop 60 (discussed above) can be used in this embodiment as well. Again, it is contemplated that dorsi-flexion control member 110 could be elastic or non-elastic, thus providing either the dynamic or static control mentioned above. Further, this embodiment provides the desired levels controlled resistance and stability discussed above. This embodiment again spans between upper boot 20 and lower boot 30, while also providing at least two connection points on either side of the above mentioned AFO rear centerline. In certain situations, it is contemplated that the "Y" shape could also be used in an upright orientation (i.e. non-inverted).

Figure 9:
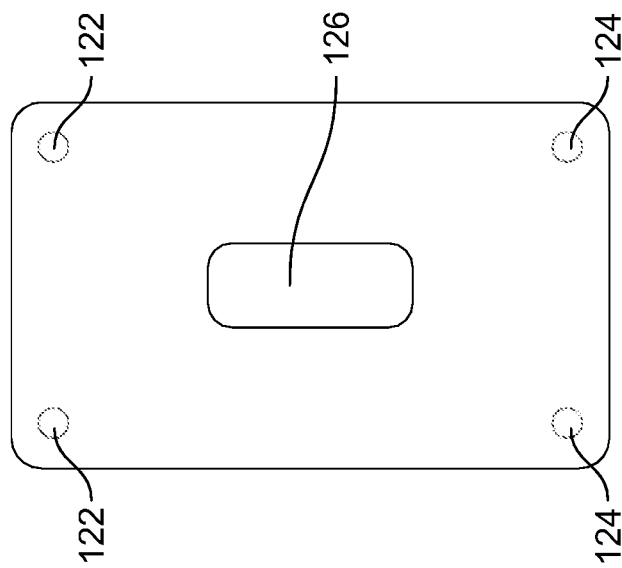
FIG. 9 is a front view of the tension device used in the second alternative embodiment of FIG. 8, shown alone.
Figure 8:
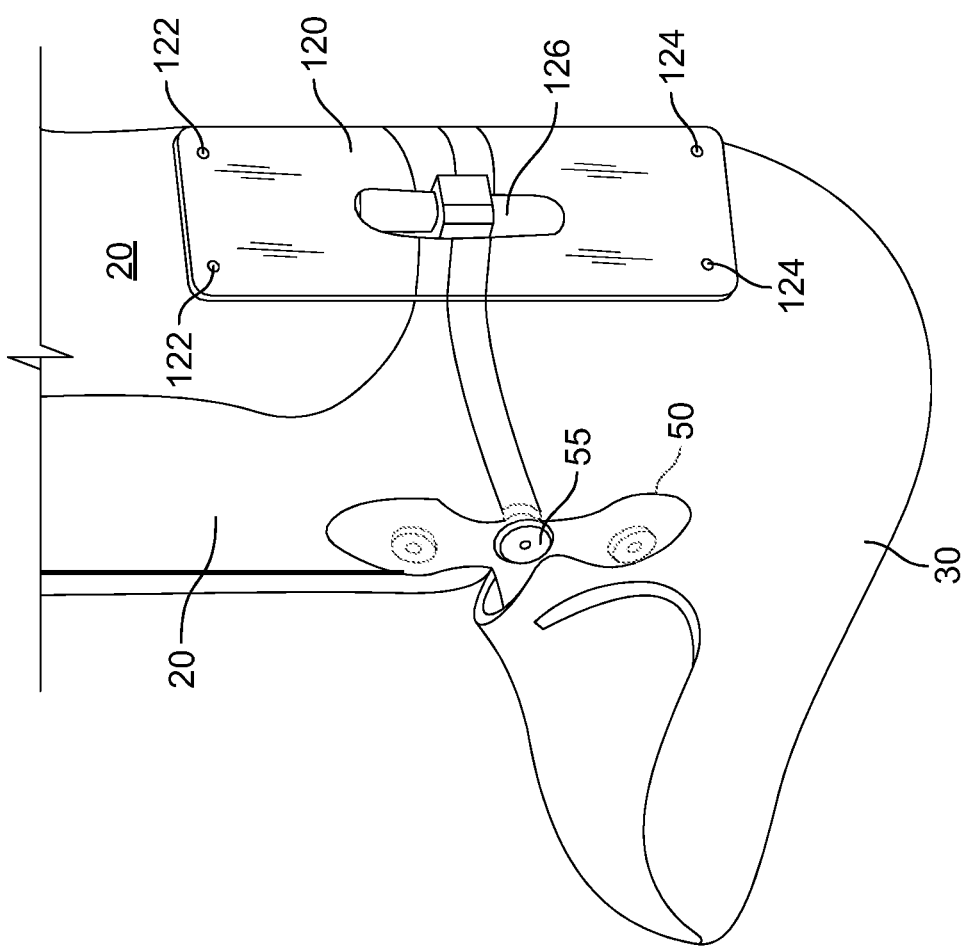
FIG. 8 is a close up view of a second alternative embodiment of the motion control system.

FIGS. 8 & 9 show a similar configuration, where another embodiment of dorsi-flexion control member 120 has a substantially rectangular shape. Again, this embodiment of dorsi-flexion control member 120 had two upper connection points 122 and two lower connection points 124, which are used for attachment to upper boot member 20 and lower boot member 30, respectively. An opening 126 in a central portion of dorsi-flexion control member 120, which is specifically configured to further accommodates the use of stop 60. As with the other embodiments, dorsi-flexion control member 120 of FIGS. 8 & 9 could be elastic or non-elastic, thus providing either the dynamic or static control mentioned above. Once again, this embodiment provides the preferred level of controlled resistance and stability discussed above.

While certain embodiments of an AFO 10 having a specific dorsi-flexion control member have been discussed above, it is clear that other variations could be possible. In use, dorsi-flexion control member 100, 110, 120 is removably attachable to AFO 10 at multiple contact points to provide tailored control. In each case, dorsi-flexion control member 100, 110, 120 is illustrated as being a generally planar plate-like structure. As shown in the figures the use of this planar plate-like structure which helps to minimize the profile of this component when coupled to the rear of the AFO Again, it is generally contemplated that this would include alignment along the center-rear portion of the AFO, to provide support that is perpendicualarly aligned with hinge point 55. That said, there may be instances where different types of alignment are appropriate. Further, the configuration and placement of attachment points may be altered or modified, thereby adjusting the way forces are distributed.

In addition to the alternatives outlined above, it is contemplated that dorsi-flexion control member 100 could be made up of separate components, as needed. For example, dorsi-flexion control member could be configured as a matched pair of strips added to the rear of the AFO. In this configuration, each strip would have selected elastic characteristics, thus providing the level of support and stability discussed above. All of these variations and considerations are considered to be within the scope of the dorsi-flexion control concepts contemplated for use with an AFO.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. An articulated Ankle Foot Orthosis (AFO) providing tailored dorsi-flexion support for a user's ankle, comprising:
an articulated boot configured to surround an ankle portion of a foot of the user, the articulated boot having an upper boot member and a lower boot member and a hinge component rotatably coupling the upper boot member and the lower boot member and configured to be positioned adjacent the user's ankle to allow dorsi-flexion movement of the user's ankle in a sagittal plane about a hinge axis; and
a planar elongated plate-shaped dorsi-flexion control member formed of a selected material having a predetermined elastic characteristic, the dorsi-flexion control member coupled at an upper portion thereof to the upper boot member and coupled at a lower portion thereof to the lower boot member to provide a predetermined level of resistance to the dorsi-flexion movement, the dorsi-flexion control member having a pair of upper connection points and a pair of lower connection points, wherein the pair of upper connection points are coupled to the upper boot member at a corresponding first upper connection location and a corresponding second upper connection location which are on either side of a rear AFO centerline axis, and the pair of lower connection points are coupled to the lower boot member at a first lower connection location and a second lower connection location which are on either side of the rear AFO centerline, with the first upper connection location and the first lower connection location being on a first side of and equidistant from the AFO centerline, and the second upper connection location and the second lower connection location being on a second side of and equidistant from the AFO centerline, wherein the dorsi-flexion control member bridges a gap between the upper boot and the lower boot, the plate-shaped dorsi-flexion control member configured to conform to an adjacent portion of the boot, wherein the dorsi-flexion control member provides the predetermined level of resistance depending on a thickness of the dorsi-flexion control member and the predetermined elastic characteristic of the selected material, and wherein the dorsi-flexion control member further has a hole in a central portion thereof through which a stop member protrudes from a rear portion of the upper boot member or the lower boot member, wherein the hole extends between points above and below the gap between the upper boot member and lower boot member.

2. The articulated Ankle Foot Orthosis (AFO) of claim 1 wherein the elastic characteristic is controllable by providing a selected configuration and selected materials to form the dorsi-flexion control member.

3. The articulated Ankle Foot Orthosis (AFO) of claim 2 wherein the thickness of the dorsi-flexion control member is predetermined, which controls the elastic characteristic.

4. The articulated Ankle Foot Orthosis (AFO) of claim 3 wherein the dorsi-flexion control member is X-shaped having a pair of upper arms supporting the upper connection points and a pair of lower arms supporting the lower connection points.

5. The articulated Ankle Foot Orthosis (AFO) of claim 3 wherein the predetermined thickness is in a range of one-sixteenth (1/16) of an inch to one-quarter (1/4) of an inch.

6. The articulated Ankle Foot Orthosis (AFO) of claim 1 wherein the first upper connection location and the second upper connection location are equidistant from the hinge axis, and the first lower connection location and the second lower connection location are equidistant from the hinge axis.

7. A dorsi-flexion control member attachable to an articulated Ankle Foot Orthosis (AFO) which has an upper boot member and a lower boot member which are hingeably coupled to one another to allow articulation about an ankle joint axis and thereby allow dorsi-flexion and plantar-flexion of a user's ankle in a sagittal plane, the dorsi-flexion control member comprising:
 a planar elongated plate-shaped main body having a predetermined thickness and an elongate X-shape with a pair of upper arms, a pair of lower arms and a central portion, with the pair of upper arms extending from the central portion and the pair of lower arms extending from the central portion in a direction opposite the pair of upper arms, the central portion having a central aperture therein through which a stop member protrudes from a rear portion of the upper boot member or the lower boot member, wherein the central aperture extends between points above and below a separation between the upper boot member and lower boot member;
 wherein the pair of upper arms are configured to be attachable to the upper boot member at a corresponding first upper boot attachment location and a corresponding second upper boot attachment location which are configured to be situated on opposite sides of the sagittal plane, and the pair of lower arms are configured to be attachable to the lower boot member at a corresponding first lower attachment location and a corresponding second lower boot attachment location which are also configured to be on opposite sides of the sagittal plane, and wherein the first upper attachment location and the first lower attachment location are configured to be equidistant from the sagittal plane and wherein the second upper attachment location and the second lower attachment location are configured to be equidistant from the sagittal plane, the plate-shaped main body conforming to an adjacent portion of the AFO;
 wherein the main body is formed of an elastic material with a predetermined elastic characteristic, with the elastic characteristic, the predetermined thickness and the elongate X-shape of the main body configured to provide controlled resistance to dorsi-flexion in the sagittal plane in a manner that causes a pair of resistive forces between the upper boot member and the lower boot member to be situated on both sides of the sagittal plane.

8. The dorsi-flexion control member of claim 7 wherein the central aperture is configured in an elongate form.

9. The dorsi-flexion control member of claim 8 wherein the X-shaped main body further comprises a shape having a pair of side indentations, an upper indentation and a lower indentation.

10. The dorsi-flexion control member of claim 9 wherein the pair of side indentations are arcuate having a first radius, while the upper indentation and the lower indentation are also arcuate with a second radius, wherein the first radius and the second radius are unequal.

11. The dorsi-flexion control member of claim 7 wherein the predetermined thickness is in a range of one-sixteenth (1/16) of an inch to one-quarter (1/4) of an inch.

12. An articulated Ankle Foot Orthosis (AFO) for providing dorsi-flexion support for a user, comprising:
 a boot configured to surround an ankle portion of a foot of the user, the boot having an upper boot member and a lower boot member and a hinge structure rotatably coupling the upper boot member and the lower boot member thus being configured to allow dorsi-flexion and plantar-flexion of the user's ankle in a sagittal plane about a hinge axis; and
 a dorsi-flexion control member removably coupleable to a rear portion of the boot, the dorsi-flexion control member having a planar elongated plate-shaped main body formed of an elastic material having a predetermined elastic characteristic, the main body of the dorsi-flexion control member having an upper portion coupleable to the upper boot member at a first upper connection point and a second upper connection point and having a lower portion coupleable to the lower boot member at a first lower connection point and a second lower connection point, wherein the plate-shaped main body conforms to adjacent portions of the upper boot member and the lower boot member and bridges a gap between the upper boot member and the lower boot member;
 wherein the dorsi-flexion control member is positioned along and across a rear vertical centerline of the boot with the first upper connection point and the second upper connection point being located on either side of the centerline, and the first lower connection point and the second lower connection point being located on either side of the centerline;
 wherein the first upper connection point and the first lower connection point are equidistant from the centerline, and the second upper connection point and the second lower connection point are equidistant from the centerline, to thereby provide balanced resistance to motion within the sagittal plane, wherein forward dorsi-flexion movement is configured to create shear forces along the main body of the dorsi-flexion control member thereby providing resistance to the dorsi-flexion movement of the user's ankle, wherein an amount of resistance is dependent upon a thickness and the predetermined elastic characteristic of the material forming the dorsi-flexion control member; and wherein the dorsi-flexion control member has a central hole therein through which a stop member protrudes from a rear portion of the upper boot member or the lower boot member, wherein the hole extends between points above and below the gap between the upper boot member and lower boot member.

13. An articulated Ankle Foot Orthosis (AFO) of claim 12, wherein the dorsi-flexion control member is configured as an elongated X-shaped structure with a pair of upper arms and a pair of lower arms, with a connection structure on each of the upper arms aligning with the upper connection points and a connection structure on each of the pair of lower arms aligning with the lower connection points, the dorsi-flexion control member further attached at the pair of upper connection points on the upper boot member which are configured to be positioned on either side of the sagittal plane and attached at the pair of lower connection points on the lower boot member which are configured to be positioned on either side of the sagittal plane.

14. The articulated Ankle Foot Orthosis (AFO) of claim 12 wherein the thickness is predetermined and is in a range of one-sixteenth (1/16) of an inch to one-quarter (1/4) of an inch.

15. The articulated Ankle Foot Orthosis (AFO) of claim 12, wherein the dorsi-flexion control member is rectangular.

16. The articulated Ankle Foot Orthosis (AFO) of claim 12 wherein the first upper connection point and the second upper connection point are equidistant from the hinge axis, and wherein the first lower connection point and the second lower connection point are equidistant from the hinge axis.

* * * * *

UNITED STATES PATENT AND TRADEMARK OFFICE
CERTIFICATE OF CORRECTION

| | |
|---|---|
| PATENT NO. | : 11,963,897 B2 |
| APPLICATION NO. | : 16/959613 |
| DATED | : April 23, 2024 |
| INVENTOR(S) | : Patrick Scott Hinshon |

It is certified that error appears in the above-identified patent and that said Letters Patent is hereby corrected as shown below:

In the Claims

In Claim 12 at Column 8, Line 28, delete "fora" and insert -- for a --.

Signed and Sealed this
Eleventh Day of June, 2024

Katherine Kelly Vidal
*Director of the United States Patent and Trademark Office*